(12) United States Patent
Swab

(10) Patent No.: US 6,765,185 B2
(45) Date of Patent: Jul. 20, 2004

(54) COMPUTER VISION RECOGNITION OF METALLIC OBJECTS AGAINST A POORLY CONTRASTING BACKGROUND

(75) Inventor: Michael Thomas Swab, Acworth, GA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/970,960

(22) Filed: Oct. 4, 2001

(65) Prior Publication Data
US 2003/0066952 A1 Apr. 10, 2003

(51) Int. Cl.[7] .............................................. H01L 27/00
(52) U.S. Cl. .................. 250/208.1; 250/225; 250/559.4
(58) Field of Search ............................. 250/208.1, 225, 250/559.34, 559.09, 559.04; 356/237.2, 237.5; 348/126

(56) References Cited

U.S. PATENT DOCUMENTS

| | | | | |
|---|---|---|---|---|
| 4,669,875 A | * | 6/1987 | Shiba et al. | 356/237.3 |
| 5,426,506 A | * | 6/1995 | Ellingson et al. | 356/369 |
| 5,459,794 A | * | 10/1995 | Ninomiya et al. | 382/145 |
| 5,974,160 A | * | 10/1999 | Shiratori et al. | 382/112 |
| 6,201,892 B1 | * | 3/2001 | Ludlow et al. | 382/149 |
| 6,538,750 B1 | * | 3/2003 | Fishbaine et al. | 382/151 |
| 2002/0125411 A1 | * | 9/2002 | Christy | 250/225 |

OTHER PUBLICATIONS

IBM Entitled: "Ceramic Ball Grid Array Surface Mount Assembly and Rework" Jul. 2000. http://www–3.ibm.com/chips/techlib/techlib.nsf/techdocs/852569B20050FF7785256996005B1D23/$file/bgaguide.pdf.

* cited by examiner

Primary Examiner—Que T. Le
(74) Attorney, Agent, or Firm—Jack D. Slobod

(57) ABSTRACT

The contrast between solder balls and substrate of a Ball Grid Array (BGA) as visualized by a camera of a computer vision system is improved sufficiently to enable reliable recognition in the poor contrast situation when the balls are silver colored and the substrate background is white or light colored by illuminating the BGA with polarized light, and the camera viewing the light reflected from the BGA via a polarization filter oriented to not pass light reflected from the solder balls but to pass light reflected from the substrate.

20 Claims, 1 Drawing Sheet

COMPUTER VISION RECOGNITION OF METALLIC OBJECTS AGAINST A POORLY CONTRASTING BACKGROUND

BACKGROUND OF THE INVENTION

1. Field of the Invention

The present invention relates to visualization of parts having metallic objects against a dielectric or non-metallic poorly contrasting background. The invention is particularly, but not exclusively, useful for recognizing by computer vision a Ball Grid Array (BGA) of small solder balls carried by a light colored ceramic substrate for the purposes of inspection and surface mounting the BGA on a circuit board or card.

2. Description of the Related Art

Typical Ball Grid Arrays (BGAs) are described in IBM Application Note, "Ceramic Ball Grid Array Surface Mount Assembly and Rework", July 2000.

In such publication, at page 10, it is indicated that in the case of BGA packages employing a white ceramic substrate, poor lighting contrast between the solder balls and the white ceramic substrate may make it difficult to tune a vision system, causing failure to properly recognize BGA packages and erroneous rejections.

A BGA or Ceramic Ball Grid Array (CBGA) is a commonly used component or package in Surface Mount Technology (SMT). The bottom of the part is formed by high melt small (e.g. a fraction of a mm in diameter) solder balls arranged in a predetermined, typically rectangular grid array, pattern on a ceramic substrate to which they are joined by eutectic solder fillets. The part is placed on a circuit board or card that has a matching pattern of contact pads on which eutectic solder paste has been applied. The circuit board or card is then run through an oven such that the solder paste forms fillets joining the solder balls to the contact pads.

Currently, a pick and place machine is used to pick the BGA, along with other parts, out of a storage location, and computer vision equipment, including an upwardly looking camera and frontal lighting, is employed by the pick and place machine to inspect the BGA, and if the BGA is not rejected, to steer the placement of the BGA on the circuit board or card with proper registration of the BGA balls to the circuit pads of the board or card. The BGA should be rejected if it has one or more missing balls, incorrect ball spacing, or nonsymmetrical ball size.

Most BGAs have a dark colored ceramic bottom and silver colored metallic balls. This combination provides excellent contrast between balls and background. Some BGAs have silver or gold colored metallic balls on a white or very light colored ceramic background. These parts do not provide sufficient visual contrast for current computer vision systems to reliably recognize the BGA. Specifically, when recognition using current camera and lighting is done on BGAs having a white or light colored bottom, the vision system cannot distinguish between balls and background because the balls appear almost as bright as the ceramic background.

One known technique used to attempt to improve the visualization and, as a result the recognition, of white ceramic BGAs, involves illuminating the part being visualized by so-called "coaxial lighting" wherein the illuminating light is introduced via a beam splitter in front of the camera lens so that the resulting illumination is coaxial with the lens of the camera. The use of such coaxial lighting has proven to be marginally effective at best. When coaxial lighting is used in combination with a rather expensive telecentric camera lens, a higher, but still substandard, level of successful recognition is achieved.

OBJECTS AND SUMMARY OF THE INVENTION

It is an object of the present invention to overcome the aforementioned deficiencies in the prior art visualization of metallic objects against a poorly contrasting dielectric background, and in particular to improve the visualization, and thus the rate of successful recognition, of white or light colored ceramic BGAs.

This and other objects of the present invention are satisfied by a method and apparatus in which the part being visualized is illuminated by linearly polarized electromagnetic radiation, e.g light passed through a polarization filter, and an image is formed of the electromagnetic radiation reflected from the part and passed through a polarization filter oriented to pass radiation having a polarization direction that is substantially orthogonal to the direction of polarization of the radiation illuminating the part. Because the radiation is reflected from the metallic objects or solder balls with the same polarization direction as the illuminating radiation, substantially no radiation reflected from the metallic objects passes through the latter polarization filter and appears in the formed image. On the other hand, because radiation reflected from the non-metallic or dielectric background is smeared in polarization and includes radiation with a polarization direction that is orthogonal to the polarization direction of the illuminating radiation, some radiation reflected from the background passes through the latter polarization filter and appears in the formed image. Consequently, the part is visualized in the formed image with a substantial contrast between metallic objects and background, e.g. the metallic objects appear black, whereas the background appears white or light colored, allowing for reliable computer vision recognition of the metallic objects.

A method in accordance with the invention for visualization of a part having metallic objects against a light colored non-metallic background comprises illuminating the part with electromagnetic radiation that is linearly polarized in a predetermined first direction, and forming an image of electromagnetic radiation reflected from the part viewed through a linear polarization filter oriented for passing electromagnetic radiation that is linearly polarized in a second direction that is substantially orthogonal to the first polarization direction. Such method further comprises recognizing the metallic object in the formed image.

Similarly, an apparatus in accordance with the present invention for visualization of a part having metallic objects against a light colored non-metallic background comprises one or more sources for illuminating the part with electromagnetic radiation that is linearly polarized, at least one of the sources producing electromagnetic radiation that is linearly polarized in a predetermined first direction, and an image forming device for forming an image of electromagnetic radiation reflected from the part viewed through a linear polarization filter oriented for passing electromagnetic radiation that is linearly polarized in a second direction that is substantially orthogonal to the first direction. Such apparatus further comprises a computer vision system for recognizing the metallic objects in the formed image, and still further comprises a manipulator for positioning the part on a circuit board or card with recognized metallic objects of the part in registration with contact pads of the board or card.

The invention also comprises a circuit board or card on which is surface mounted a part that has been recognized in accordance with the aforementioned method, such surface mounting being with recognized metallic objects of the part in registration with contact pads of the board or card.

Other objects, features and advantages of the present invention will become apparent upon perusal of the following detailed description when taken in conjunction with the appended drawing, wherein:

DETAILED DESCRIPTION OF THE PREFERRED EMBODIMENTS

Figure 1:
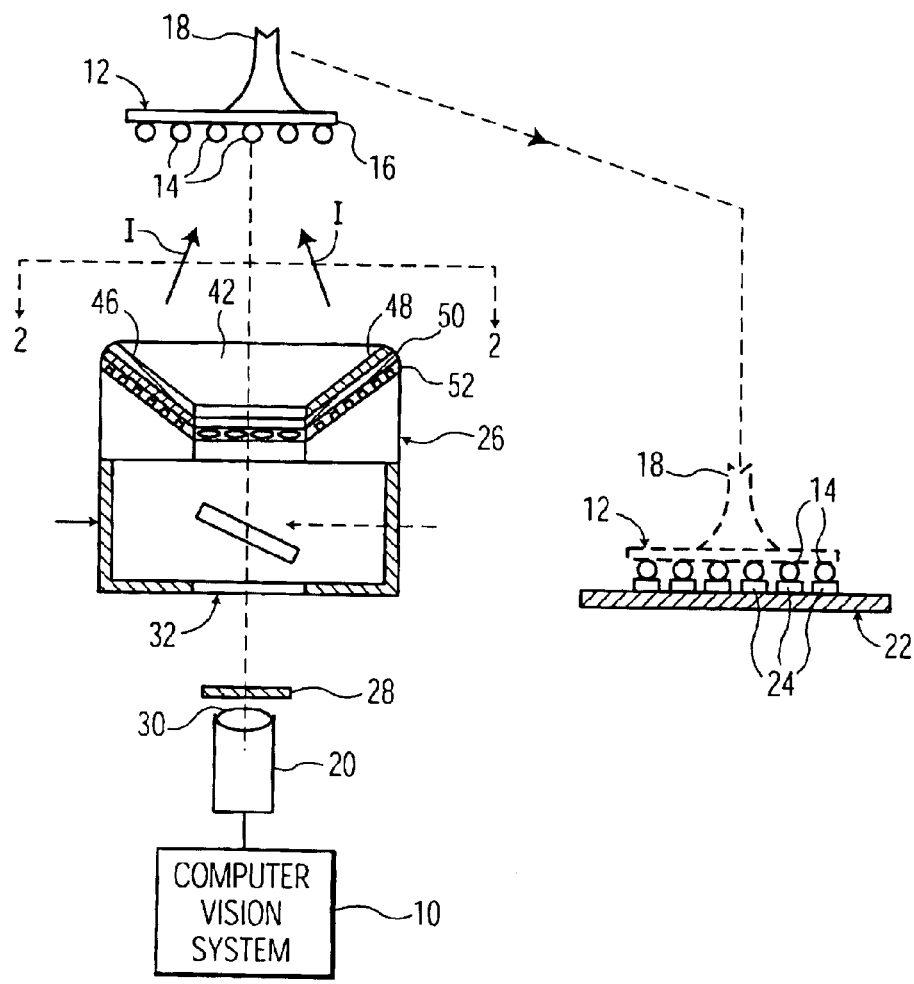
FIG. 1 is a schematic elevational cross-section view of visualization, recognition and placement apparatus in accordance with the invention.
Figure 2:
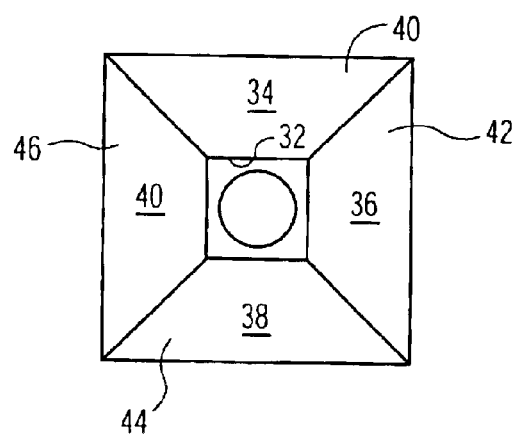
FIG. 2 is a top view of illumination and reption parts of FIG. 1, as viewed from the lines 2—2.

Referring to FIGS. 1 and 2 of the drawing, the present invention for visualization of parts having metallic objects against a dielectric or non-metallic poorly contrasting background, is explained in conjunction with a conventional computer vision system 10 recognizing a usually two dimensional Ball Grid Array (BGA) 12 of small high melt solder balls 14 carried by a ceramic dielectric substrate 16. BGA 12 is held by a gripper or manipulator 18 of a pick and place machine (not shown) over an upwardly looking camera 20 of computer vision system 10. The camera 20 forms and provides an electronic image to computer vision system 10, which system utilizes the electronic image to recognize and inspect the solder balls 14 of the BGA 12, as to existence, size and spacing. If the BGA 12 passes inspection, the vision system 10 steers the translation and placement of BGA 12 by manipulator 18 on a circuit board or card 22, with the recognized solder balls 14 of the BGA in registration with contact pads 24 of the board or card 22. As is conventional, prior to placement of the BGA 12 and other surface mount components on the circuit board or card 22 the contact pads 24 are coated with a eutectic solder paste, and after the placement of the BGA 12 and other surface mount components on circuit board or card 22, heat is applied to card with placed BGA and other components to fuse the solder paste into fillets (not shown) firmly surface mounting the BGA to the circuit board or card.

In the poorest contrast situation when the solder balls 14 are silver colored and the substrate 16 is white or light colored, the light box 26 is used to provide generally upwardly and inwardly directed polarized illumination I of BGA 12, in conjunction with a polarization filter 28 in front of the lens 30 of camera 20, in order to allow for proper visualization by camera 20, and proper recognition by vision system 10 of solder balls 14. A preferred embodiment of light box 26 has a central aperture 32 through which camera 20 looks upward via polarization filter 28, and four upwardly and outwardly inclined trapezoidal faces 34, 36, 38, 40 of a frusto-pyramid, each face forming a separate source of polarized light. The faces 34, 36, 38, and 40 comprise polarization filters 40, 42, 44, and 46 over respective milk glass diffuser panels 50, over LED arrays 52. With the direction of linear polarization passed by polarization filter 28 taken as 0°, polarization filters 40 and 44 are oriented to pass linear polarization directed at 90° and polarization filters 42 and 46 are oriented to pass linear polarization directed at 180°. The result is that the downwardly directed component of light from the four sources reflected from the solder balls 14 has a polarization at 90°, which is, or is nearly, orthogonal with the polarization direction that would be passed by polarization filter 28. Therefore no light reflected by solder balls 14 reach the lens 30 of camera 20. On the other hand, the downwardly directed component of light reflected from the white or light colored substrate 16 is substantially uniformly distributed in polarization and a substantial amount of light reflected downward from the substrate 16 passes through polarization filter 28 and reaches the lens 30 of camera 20. As a result, in the electronic image formed by camera 20, the solder balls 14 appear substantially black and the substrate 16 appears substantially white, providing good contrast for reliable recognition of solder balls 14. This contrast producing effect is thought to be due to a preservation of polarization in reflection of electromagnetic radiation from shiny metal objects versus a the smearing of polarization in reflection of electromagnetic radiation from dielectric objects.

It should now be appreciated that the objects of the present invention have been satisfied. While the present invention has been described in particular detail, it should also be appreciated that numerous modifications are possible within the intended spirit and scope of the invention. In interpreting the appended claims it should be understood that:

a) the word "comprising" does not exclude the presence of other elements or steps than those listed in a claim;

b) the word "a" or "an" preceding an element does not exclude the presence of a plurality of such elements.

c) any reference signs in the claims do not limit their scope; and d) several "means" may be represented by the same item of hardware or software implemented structure or function.

What is claimed is:

1. A method by which a pick and place machine visualizes a part having metallic objects against a non-metallic background comprising:

illuminating the part with electromagnetic radiation polarized linearly in a predetermined first direction, and forming an image of electromagnetic radiation reflected from the part viewed through a linear polarization filter oriented for passing electromagnetic radiation that is linearly polarized in a second direction that is substantially orthogonal to the first direction;

whereby in the formed image, contrast between the metallic objects and the background is produced.

2. The method as claimed in claim 1, further comprising recognizing the metallic objects in the formed image.

3. The method as claimed in claim 1, wherein the electromagnetic radiation is light, and the image is formed by a camera.

4. The method as claimed in claim 2, wherein the electromagnetic radiation is light, the image is formed by a camera of a computer vision system, and said recognizing is performed by the computer vision system.

5. The method as claimed in claim 1, wherein the part is a ball grid array, the background is dielectric, and the metallic objects are balls arranged in an array carried by the dielectric.

6. The method as claimed in claim 2, wherein the part is a ball grid array, the background is dielectric, and the metallic objects are balls arranged in an array carried by the dielectric.

7. Apparatus for visualization of a part having metallic objects against a non-metallic background as part of a surface mount tool comprising:

one or more sources for illuminating the part with electromagnetic radiation that is linearly polarized, at least one of the sources producing electromagnetic radiation that is linearly polarized in a predetermined first direction, and an image forming device for forming an image of electromagnetic radiation reflected from the part viewed through a linear polarization filter oriented for passing electromagnetic radiation that is linearly polarized in a second direction that is substantially orthogonal to the first direction, whereby in the formed image, contrast between the metallic objects and the background is produced.

8. The apparatus as claimed in claim 7, further comprising a computer vision system for recognizing the metallic objects in the formed image.

9. The apparatus as claimed in claim 7, wherein the electromagnetic radiation is light, and the image forming device is a camera.

10. The apparatus as claimed in claim 8, wherein the electromagnetic radiation is light, and the image forming device is a camera of the computer vision system.

11. The apparatus as claimed in claim 7, wherein the part is a ball grid array, the background is dielectric, and the metallic objects ate balls arranged in an array carried by the dielectric.

12. The apparatus as claimed in claim 8, wherein the part is a ball grid array, the background is dielectric, and the metallic objects are balls arranged in an array carried by the dielectric.

13. The apparatus as darned in claim 8, further comprising a manipulator for positioning the part on a circuit board or card with recognized metallic objects of the part in registration with contact pads of the board or card.

14. The apparatus as claimed in claim 12, further comprising a manipulator for positioning the ball grid array on a circuit board or card with recognized balls of the ball grid array in registration with contact pads of the board or card.

15. The method of claim 2, further comprising: mounting a part recognized in registration with contact pads of one of a circuit board or a circuit card.

16. The method of claim 6, further comprising: surface mounting said recognized part in registration with contact pads of one of a circuit board or a circuit card.

17. A pick and place machine that utilizes an automated visualization system to inspect and place surface mount components on a work surface, comprising:

(a) a manipulator operable to select a surface mount component; and (b) a visualization system wherein said manipulator is operable to position said surface mount component relative to said visualization system, wherein said visualization system includes (i) a means for illuminating said surface mount component with electromagnetic radiation polarized in a first direction;

(ii) an optical filter that passes electromagnetic radiation scattered by said surface mount component and linearly polarized ma second direction that is substantially orthogonal to said first direction; and (iii) a means for imaging said electromagnetic radiation passed by said filter.

18. The pick and place machine of claim 17, wherein said surface mount component is inspected prior to placing said surface mount component in said predetermined location, and wherein if said surface mount component fails inspection said surface mount component is rejected.

19. The pick and place machine of claim 17, wherein said work surface is a circuit board.

20. The pick and place machine of claim 17, wherein said electromagnetic radiation is linearly polarized.

* * * * *